United States Patent
Monk

(10) Patent No.: US 9,284,650 B2
(45) Date of Patent: Mar. 15, 2016

(54) QUATERNARY FATTY ACID ESTERS AS CORROSION INHIBITORS

(71) Applicant: Ecolab USA Inc., Naperville, IL (US)

(72) Inventor: Keith A. Monk, League City, TX (US)

(73) Assignee: ECOLAB USA Inc., St. Paul, MN (US)

( * ) Notice: Subject to any disclaimer, the term of this patent is extended or adjusted under 35 U.S.C. 154(b) by 107 days.

(21) Appl. No.: 14/191,983

(22) Filed: Feb. 27, 2014

(65) Prior Publication Data

US 2015/0240365 A1    Aug. 27, 2015

(51) Int. Cl.
| | |
|---|---|
| B08B 17/00 | (2006.01) |
| C23F 11/00 | (2006.01) |
| C23F 11/04 | (2006.01) |
| B08B 7/00 | (2006.01) |
| B08B 9/00 | (2006.01) |
| C23F 11/14 | (2006.01) |
| C07C 219/08 | (2006.01) |
| C07C 217/08 | (2006.01) |
| C07C 213/06 | (2006.01) |

(52) U.S. Cl.
CPC .............. *C23F 11/141* (2013.01); *C07C 213/06* (2013.01); *C07C 217/08* (2013.01); *C07C 219/08* (2013.01)

(58) Field of Classification Search
CPC .......... A61B 19/34; A61B 19/02; B05C 1/00; C23F 11/00

USPC .............. 422/6–7, 14, 16; 134/6, 22.1, 22.14, 134/22.19
See application file for complete search history.

(56) References Cited

U.S. PATENT DOCUMENTS

| | | | |
|---|---|---|---|
| 6,043,203 A | 3/2000 | Urfer et al. | |
| 6,432,895 B1 | 8/2002 | Bigorra et al. | |
| 7,087,569 B2 | 8/2006 | Lentsch et al. | |
| 7,135,448 B2 | 11/2006 | Lentsch et al. | |
| 7,196,045 B2 | 3/2007 | Lentsch et al. | |
| 7,524,803 B2 | 4/2009 | Lentsch et al. | |
| 7,759,299 B2 | 7/2010 | Smith et al. | |
| 7,858,574 B2 | 12/2010 | Smith et al. | |
| 8,021,493 B2 * | 9/2011 | Smith et al. ................. | 134/25.2 |
| 2003/0161808 A1 | 8/2003 | Bigorra Llosas et al. | |
| 2004/0180028 A1 | 9/2004 | Prat Queralt et al. | |

* cited by examiner

*Primary Examiner* — Monzer R Chorbaji
(74) *Attorney, Agent, or Firm* — Eric D. Babych; Brinks Gilson & Lione

(57) ABSTRACT

Corrosion inhibitor compositions, methods of inhibiting or reducing corrosion, and methods of manufacturing corrosion inhibitor compositions are disclosed herein. In certain methods, the corrosion inhibitor compositions may be added to an aqueous industrial system having at least one surface. The aqueous industrial system may be a water recirculating system, a cooling water system, a boiler water system, a pulp slurry, a papermaking process, a ceramic slurry, a mixed solid/liquid system, or an oil-field system. A method of manufacturing a corrosion inhibitor composition may include reacting an alkanolamine with a fatty acid to form a fatty acid ester reaction product and reacting the fatty acid ester reaction product with an alkyl halide or an acrylate.

20 Claims, No Drawings

QUATERNARY FATTY ACID ESTERS AS CORROSION INHIBITORS

BACKGROUND

1. Field of the Invention

The present disclosure generally relates to corrosion control. More particularly, the present disclosure relates to quaternary ammonium corrosion inhibitor compositions, methods of inhibiting corrosion, and methods of manufacturing quaternary ammonium corrosion inhibiting compositions.

2. Description of the Related Art

Oil and gas wells are typically subjected to numerous chemical treatments during their production life to enhance operation and protect the integrity of the asset. Corrosion of metal surfaces in aqueous media has long been a problem for the oil and gas industry. It is well-known that during the production of oil and gas several other corrosive components are present, such as brines, organic acids, carbon dioxide, hydrogen sulfide, and microorganisms. These aggressive constituents can cause severe corrosion as demonstrated by surface pitting, embrittlement, and loss of metal.

The assets are usually composed of mild steels but more expensive high alloy steels including chrome steels, ferritic alloy steels, austenitic stainless steels, precipitation-hardened stainless steels, and high nickel content steels can also be utilized. Corrosion issues are even more troublesome in deep-sea operations where replacement of corroded equipment is difficult and costly. Therefore, it is common practice to employ corrosion inhibitors during the production, transportation, storage, and separation of crude oil and natural gas.

Corrosion inhibitors are usually surface-active compounds that form protective coatings on the surface of metals and suppress corrosion by preventing or reducing contact of the corrosive species to the pipeline surface. Common corrosion inhibitors are composed of amines, condensation products of fatty acids with polyamines, imidazolines, and/or quaternary ammonium compounds. Among the most frequently used corrosion inhibitors in crude oil and natural gas extraction are imidazoline derivatives and benzyldimethylalkylammonium chlorides.

Many regions around the world are extremely conscious about the potential harmful effects of chemical use in environmentally sensitive areas. Components in such products are often evaluated for their potential to bioaccumulate in organisms, their ability to biodegrade, and their toxicity in select aquatic species. The combination of these tests allows the regional authorities to assess the potential danger to the area of interest and permit or deny the use of the chemical.

Many corrosion inhibitor formulations have components that have toxicity, bioaccumulative, and/or biodegradation problems that may pose a threat. As such, the development of new, high-performance actives that meet the stringent environmental regulations of these regions is needed.

BRIEF SUMMARY

Certain aspects of the present disclosure relate to corrosion inhibitor compositions. In one particular aspect, the corrosion inhibitor comprises the following general structure:

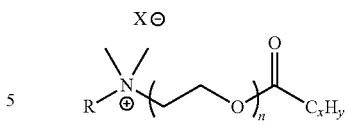

wherein n is 1 or 2; x is 1, 2, 3, 4, 5, 6, 7, 8, 9, 10, 11, 12, 13, 14, 15, 16, 17, 18, 19, 20, 21, or 22; y is an integer corresponding to a number of hydrogen atoms necessary for each carbon of the $C_xH_y$ group to form four covalent bonds; R is H, a benzyl group, a linear alkyl group, or a branched alkyl group; and $X^-$ is an anion.

Other aspects of the present disclosure relate to methods of inhibiting or reducing corrosion. In one particular aspect, a method of inhibiting corrosion is comprises the steps of adding an effective amount of a corrosion inhibitor composition comprising a hydrolysable functional group to an aqueous industrial system having at least one surface, and inhibiting corrosion of the at least one surface.

Still other aspects of the present disclosure relate to methods of manufacturing corrosion inhibitor compositions. In one particular aspect, a method of manufacturing a quaternary ammonium corrosion inhibitor composition comprises the steps of reacting an alkanolamine with a fatty acid in a reaction vessel to form a fatty acid ester reaction product, and reacting the fatty acid ester reaction product with an alkyl halide or acrylate.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

BRIEF DESCRIPTION OF THE SEVERAL VIEWS OF THE DRAWINGS

Not applicable.

DETAILED DESCRIPTION

Various embodiments are described below. The relationship and functioning of the various elements of the embodiments may better be understood by reference to the following detailed description. However, embodiments are not limited to those explicitly described below.

The present disclosure relates to corrosion inhibitor compositions, methods of manufacturing the corrosion inhibitor compositions, and methods of inhibiting corrosion. While sections of the present disclosure may refer to a "corrosion inhibitor," it is to be understood, unless specified to the contrary, that a "corrosion inhibitor" or "corrosion inhibitor composition" may comprise a single corrosion inhibiting compound or may comprise a mixture of two or more corrosion inhibiting compounds.

A corrosion inhibitor according to the present disclosure may comprise a hydrolysable functional group. Illustrative, non-limiting examples of hydrolysable functional groups are carboxylic esters and amides that can yield carboxylic acid products. Sugars can also be hydrolyzed through the cleavage of ether bonds. Other common functional groups that may be hydrolyzed include phosphate esters and imidazolines. Having the hydrolysable functionality incorporated into the molecular structure of the corrosion inhibitor composition allows cleavage and enhanced degradation under certain industrial conditions. The presently disclosed corrosion inhibitor compositions also have an improved toxicological profile when compared to currently available quaternary ammonium chlorides, such as those used in the oil field industry.

In certain aspects of the present disclosure, the corrosion inhibitor composition (or surface-active intermediate) is obtained through a condensation reaction with an alkanolamine and a fatty acid, followed by quaternization with an alkyl halide. The general reaction is depicted below:

Scheme 1

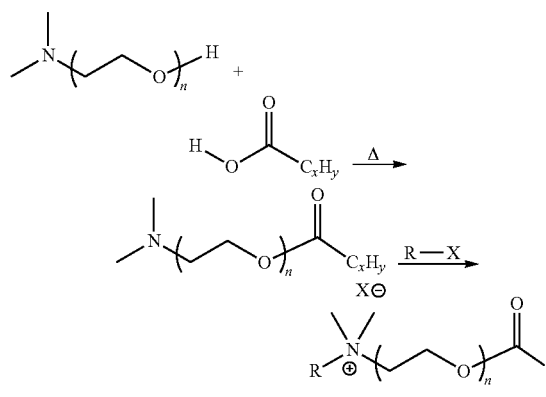

In the compounds depicted in Scheme 1, R may be a linear alkyl group, a branched alkyl group, a benzyl group, or a hydrogen (which may be obtained by neutralization with an acid, for example). Illustrative, non-limiting examples are ethyl, n-butyl, ethylacetate, and propanediol. The variable "n" can be any number, such as 1, 2, 3, 4, or 5. In some aspects, n is 1 or 2. The variable "$X^-$" can be any negatively charged ion (anion), such as $I^-$, $Cl^-$ or $Br^-$.

The portion or group of the composition defined as "$C_xH_y$" may be hydrophobic. The "$C_xH_y$" group of the composition may be a linear alkyl group, a branched alkyl group, a cyclic alkyl group, a saturated alkyl group, or an unsaturated alkyl group. The "$C_xH_y$" group may comprise from about 1 to about 22 carbon atoms. In some aspects, the "$C_xH_y$" group comprises from about 12 to about 18 carbon atoms.

The total number of hydrogen atoms (i.e. the variable "y") will depend upon the configuration of the "$C_xH_y$" group but in any event, the number of hydrogen atoms present will be whatever amount is necessary to be sure that each carbon atom in the "$C_xH_y$" group forms a total of four covalent bonds. For example, if the "$C_xH_y$" is a cyclobutyl group as follows:

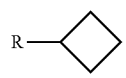

then it would have 7 hydrogen atoms (y=7). If the "$C_xH_y$" is a linear butyl group as follows:

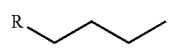

then it would have 9 hydrogen atoms. If the "$C_xH_y$" is a tertiary butyl group as follows:

then it would have 10 hydrogen atoms. The foregoing examples of "$C_xH_y$" groups are only for purposes of illustration. These may not be the preferred "$C_xH_y$" groups and any other "$C_xH_y$" group may be used as described above. The foregoing examples are only given to indicate that the number of hydrogen atoms will vary, even if the number of carbon atoms in the "$C_xH_y$" remains the same.

In some aspects, the number of carbon atoms (or "x") ranges from about 12 to about 18 and the number of hydrogen atoms (or "y") ranges from about 29 to about 35. Illustrative, non-limiting examples of "$C_xH_y$" groups may be any group selected from $C_{17}H_{35}$, $C_{17}H_{33}$, $C_{17}H_{31}$, $C_{17}H_{29}$, $C_{15}H_{31}$, $C_{15}H_{29}$, $C_{13}H_{27}$, $C_{13}H_{25}$, and $C_{11}H_{23}$.

The final product of Scheme 1 is a quaternary fatty acid ester corrosion inhibitor. Illustrative, non-limiting examples of quaternary fatty acid ester corrosion inhibiting compositions according to the present disclosure may be selected from:

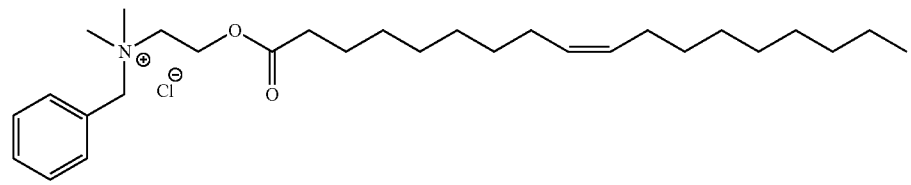 [SMILES: CCCCCCCC/C=C\CCCCCCCC(=O)OCC[N+](C)(C)Cc1ccccc1 ; [Cl-]]

mono((Z)-N-benzyl-N,N-dimethyl-2-(oleoyloxy)ethanaminium)hexachloride;

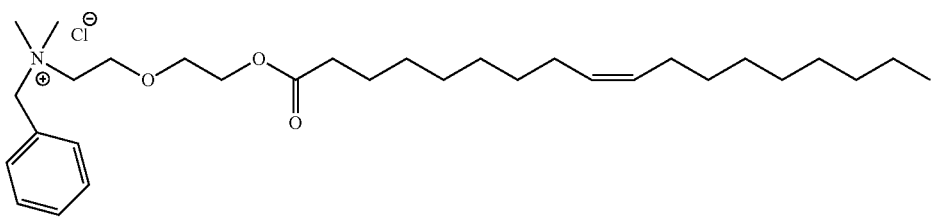 [SMILES: CCCCCCCC/C=C\CCCCCCCC(=O)OCCOCC[N+](C)(C)Cc1ccccc1 ; [Cl-]]

(Z)-N-benzyl-N,N-dimethyl-2-(2-(oleoyloxy)ethoxy)ethanaminium chloride;

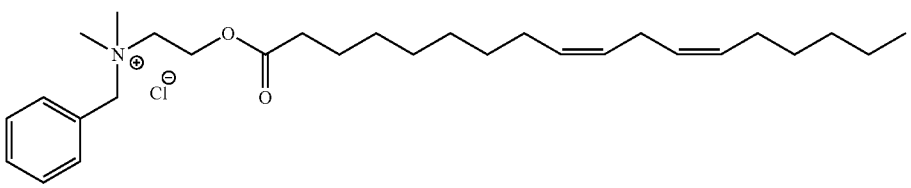 [SMILES: CCCCC/C=C\C/C=C\CCCCCCCC(=O)OCC[N+](C)(C)Cc1ccccc1 ; [Cl-]]

N-benzyl-N,N-dimethyl-2-((9Z,12Z)-octadeca-9,12-dienoyloxy)ethanaminium chloride;

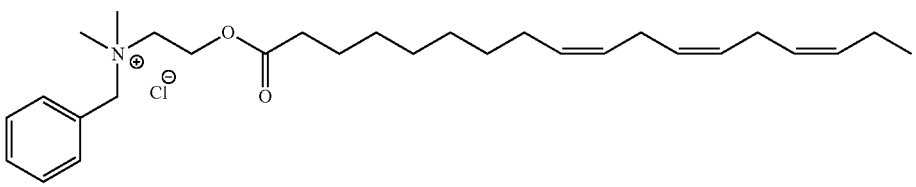 [SMILES: CC/C=C\C/C=C\C/C=C\CCCCCCCC(=O)OCC[N+](C)(C)Cc1ccccc1 ; [Cl-]]

N-benzyl-N,N-dimethyl-2-((9Z,12Z,15Z)-octadeca-9,12,15-trienoyloxy)ethanaminium chloride;

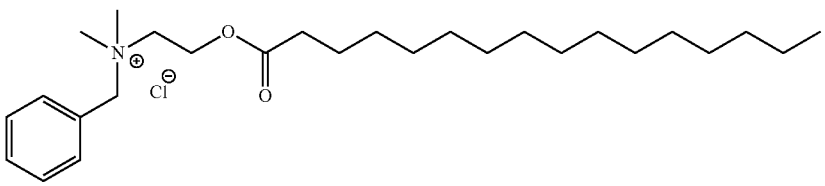 [SMILES: CCCCCCCCCCCCCCCC(=O)OCC[N+](C)(C)Cc1ccccc1 ; [Cl-]]

N-benzyl-N,N-dimethyl-2-(palmitoyloxy)ethanaminium chloride;

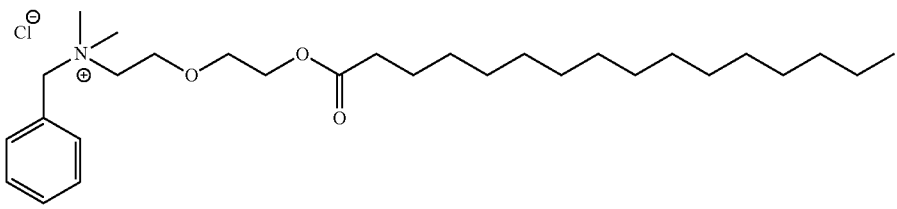 [SMILES: CCCCCCCCCCCCCCCC(=O)OCCOCC[N+](C)(C)Cc1ccccc1 ; [Cl-]]

N-benzyl-N,N-dimethyl-2-(2-(palmitoyloxy)ethoxy)ethanaminium chloride;

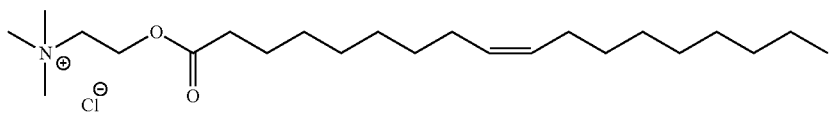 [SMILES: CCCCCCCC/C=C\CCCCCCCC(=O)OCC[N+](C)(C)C ; [Cl-]]

mono((Z)-N,N,N-trimethyl-2-(oleoyloxy)ethanaminium) dichloride;

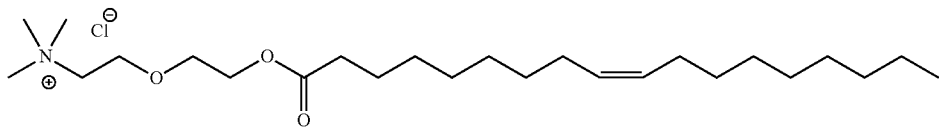 [SMILES: CCCCCCCC/C=C\CCCCCCCC(=O)OCCOCC[N+](C)(C)C ; [Cl-]]

(Z)-N,N,N-trimethyl-2-(2-(oleoyloxy)ethoxy)ethanaminium chloride;

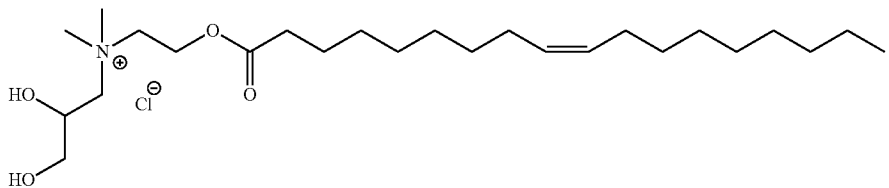 [SMILES: CCCCCCCC/C=C\CCCCCCCC(=O)OCC[N+](C)(C)CC(O)CO ; [Cl-]]

mono((Z)-2,3-dihydroxy-N,N-dimethyl-N-(2-(oleoyloxy)ethyl)propan-1-aminium)dichloride; and

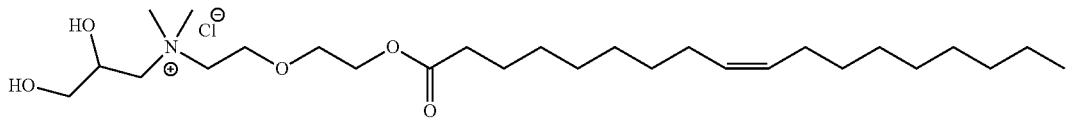 [SMILES: CCCCCCCC/C=C\CCCCCCCC(=O)OCCOCC[N+](C)(C)CC(O)CO ; [Cl-]]

(Z)-2,3-dihydroxy-N,N-dimethyl-N-(2-(2-oleoyloxy)ethoyx)ethyl)propan-1-aminium chloride.

Any alkanolamine falling under the scope of the general structure depicted in Scheme 1 may be used in accordance with the present disclosure. Illustrative, non-limiting examples of alkanolamines are 2-[2-(dimethylamino)ethoxy]ethanol and 2-dimethylaminoethanol.

Any fatty acid may be used in accordance with the present disclosure. Illustrative, non-limiting examples of fatty acids may be selected from tall oil fatty acid, soya fatty acid, oleic acid, linoleic acid, linolenic acid, coco fatty acid, stearic acid, palmitic acid, lauric acid, capric acid, myristic acid, and arachidic acid. In some aspects, the fatty acid is a fatty acid from animal and vegetable sources, which are comprised of mixtures of various chain lengths and saturation/unsaturation.

Any alkyl halide may be used in accordance with the present disclosure. Illustrative, non-limiting examples may be selected from benzyl chloride, methyl chloride, ethyl chloride, propyl chloride, butyl chloride, hexyl chloride, chloropropanediol, ethylchloroacetate, and bis(2-chloroethyl)ether. Bromide and iodide counterparts of the foregoing compounds may also be used, such as benzyl bromide and benzyl iodide.

The synthetic route depicted in Scheme 1 may be a two-step, one-pot synthesis (meaning both steps are consecutively carried out in the same reaction vessel) of ester quaternary ammonium compounds. There is an initial condensation reaction of the alkanolamine with the fatty acid to form a fatty acid ester reaction product, and the reaction product is converted to the quaternary ammonium compound thorough alkylation of the amine functionality with an alkyl halide or alkyl acrylate. In some aspects, more than one type of alkanolamine is added into the condensation reaction. In certain aspects, more than one type of fatty acid is added into the condensation reaction.

In some aspects of the present disclosure, a solvent is not used for the synthesis, e.g. the synthesis is carried out "neat." In other aspects, a solvent may be used. Illustrative, non-limiting examples of solvents are selected from isopropanol, methanol, ethanol, heavy aromatic naptha, toluene, ethylene glycol, ethylene glycol monobutyl ether (EGMBE), diethylene glycol monoethyl ether, xylene, or any combination thereof may be used to dilute. In some aspects, solvents comprising reactive groups, such as alcohols, are not used as the solvent.

Moreover, the heating denoted by the "Δ" symbol in Scheme 1 is not particularly limited to any specific temperature. During the first step of the synthesis (i.e. the condensation reaction), the reaction may be heated from about 150° C. to about 250° C. In one aspect, it may be heated from about 200° C. to about 225° C. In some aspects, a condenser may be attached to the reaction flask. The condensation reaction may last for any period of time and may be stopped at any time where it is determined that a sufficient amount of the fatty acid ester reaction product has formed. In some aspects, this period of time may be from about 3 hours to about 10 hours.

In one aspect, the period of time may be from about 5 hours to about 7 hours. Once the condensation reaction is complete, the reaction may be cooled to a temperature less than, for example, 80° C.

If it is desirable to perform a "one-pot" synthesis, then once the reaction mixture has been cooled, an alkyl halide or alkyl acrylate may be added to the reaction mixture. The mixture may be stirred at room temperature, or any temperature less than about 80° C., until all of the alkyl halide or alkyl acrylate has been added. Then, the reaction vessel may be fitted with a condenser and heated from about 100° C. to about 150° C. for a sufficient period of time to form the ester quaternary ammonium compound (corrosion inhibitor composition). The period of time may be from about 2 hours to about 6 hours. In one aspect, the period of time is from about 2.5 hours to about 3.5 hours.

In accordance with the present disclosure, the amounts of each reactant may vary based upon the reaction conditions and particular reactants used. In some aspects, about 1 equivalent of alkanolamine is added, based upon the amount of fatty acid. Furthermore, in some aspects, about 1 equivalent of the alkyl halide or alkyl acrylate may be added, based upon the amount of the fatty acid ester reaction product.

When using any of the presently disclosed corrosion inhibitor compositions in an industrial process, the amount of corrosion inhibitor composition to be added depends upon the particular application. Thus, the amount of corrosion inhibitor added to the system can widely vary. Generally, an amount of the corrosion inhibitor should be added such that corrosion is effectively inhibited or significantly reduced. In some aspects, from about 1 ppm to about 200 ppm of the corrosion inhibitor composition is added to the industrial system. In other aspects, from about 5 ppm to about 150 ppm is added to the industrial system. In still further aspects, from about 10 ppm to about 100 ppm of the corrosion inhibitor is added to the industrial system.

The presently disclosed corrosion inhibitor compositions, methods of inhibiting or reducing corrosion, and corrosion control programs can be applied to any type of industrial system, such as water recirculating systems, cooling water systems, boiler water systems, pulp slurries, papermaking processes, ceramic slurries, mixed solid/liquid systems, and oil-field applications, such as those disclosed in the background section of the present application. In general, the presently disclosed corrosion inhibitors can effectively inhibit or reduce corrosion in any type of aqueous system comprising a metallic or glass surface.

In one aspect, the metallic surface comprises mild steel but in other aspects, the metallic surface may comprise a member selected from the group consisting of mild steel, galvanized steel, aluminum, aluminum alloys, copper, copper nickel alloys, copper zinc alloys, brass, chrome steels, ferritic alloy steels, austenitic stainless steels, precipitation-hardened stainless steels, high nickel content steels, and any combination thereof.

The corrosion inhibitor composition may be added at any location in the aqueous system. The addition of the composition may be manual or it may be automatic, for example, by using chemical injection pumps. In some aspects, the corrosion inhibitor composition may be stored in a chemical storage tank and chemical injection pump associated therewith can pump the corrosion inhibitor into the aqueous system. The chemical injection pump(s) can be automatically or manually controlled to inject any amount of the corrosion inhibitor into the aqueous system.

The presently disclosed corrosion inhibitors may be utilized in industrial systems, such as three phase production systems, two phase production systems (i.e. oil & water), produced oil systems, water injection, water disposal systems, gas condensate applications, gas compressors, and both natural and artificial lift well processes. In any of these applications, the corrosion inhibitor may be injected continuously and/or in batches in dosage ranges from about 10 ppm (or low % levels in batch applications, such as about 3 to about 5%). In some aspects, for protection of pipes from corrosive species in the aqueous phase (such as salts, acid gases ($CO_2$ and $H_2S$), organic acids, and/or solids), the dosage may be less than about 100,000 ppm (~10%).

The aqueous medium in which the corrosion inhibitor compositions and/or formulations are applied to may be in contact with many different types of surfaces that are capable of corrosion. Illustrative, non-limiting examples are those surfaces in an oil and gas pipeline and/or refinery, such as separation vessels, dehydration units, gas lines, and pipelines, in addition to cooling water systems. In general, the dosage may be dependent upon the corrosivity of the system and oftentimes the water cut realized in the application.

In some aspects, the corrosion inhibitor may be injected down the annulus of a well and flushed with the appropriate solvent. In other aspects, it may be injected through suitable injection lines to areas where corrosion can occur through capillaries or umbilical lines (in many cases at the wellhead if suitable metallurgy is used downhole).

In accordance with the present disclosure, the corrosion inhibitor may be used in conjunction with other production chemicals including, but not limited to, hydrate inhibitors, scale inhibitors, asphaltene inhibitors, paraffin inhibitors, $H_2S$ scavengers, $O_2$ scavengers, emulsion breakers, foamers and de-foamers, and water clarifiers.

In particular aspects of the present disclosure, the corrosion inhibitors may be used in connection with warewashing compositions. Warewashing compositions may be used for protecting articles, such as glassware or silverware, from corrosion in a dishwashing or warewashing machine. However, it is to be understood that the warewashing compositions comprising the presently disclosed corrosion inhibitors can be available for cleaning environments other than inside a dishwashing or warewashing machine.

The corrosion inhibitor may be included in the warewashing composition in an amount sufficient to provide a use solution that exhibits a rate of corrosion and/or etching of glass that is less than the rate of corrosion and/or etching of glass for an otherwise identical use solution, except for the absence of the corrosion inhibitor. In some aspects, the use solution may include at least about 6 ppm of the corrosion inhibitor. In other aspects, the use solution may include between about 6 ppm and about 300 ppm of the corrosion inhibitor. In still further aspects, the use solution may include between about 20 ppm and about 200 ppm of the corrosion inhibitor. In the case of a warewashing composition concentrate that is intended to be diluted to a use solution, it is expected that the corrosion inhibitor may be provided at a concentration of between about 0.5 wt. % and about 25 wt. %, and between about 1 wt. % and about 20 wt. % of the concentrate.

In addition to the corrosion inhibitor, the warewashing composition and/or use solution may also include cleaning agents, alkaline sources, surfactants, chelating/sequestering agents, bleaching agents, detergent builders or fillers, hardening agents or solubility modifiers, defoamers, anti-redeposition agents, threshold agents, aesthetic enhancing agents (i.e., dye, perfume), and the like. Adjuvants and other additive ingredients will vary according to the type of composition being manufactured. It should be understood that these additives are optional and need not be included in the cleaning composition. When they are included, they can be included in an amount that provides for the effectiveness of the particular type of component.

The presently disclosed corrosion inhibitors may be used in connection with any warewashing operation or any warewashing composition, such as those warewashing compositions disclosed in U.S. Pat. No. 7,196,045, U.S. Pat. No. 7,524,803, U.S. Pat. No. 7,135,448, U.S. Pat. No. 7,759,299, U.S. Pat. No. 7,087,569, U.S. Pat. No. 7,858,574, and U.S. Pat. No. 8,021,493, the entire contents of each of these patents being expressly incorporated into the present application.

EXAMPLES

A 500 ml 3-necked round bottom flask was charged with approximately 150 grams of soy fatty acid (Cargill AP145, which is a mixture containing saturated and unsaturated fatty acids—20% C16:0, 6% C18:0, 16% C18:1, 50% C18:2, and 6% C18:3). An overhead stirring mechanism was attached to the flask and the temperature of the reaction was monitored using a J-KEM Scientific temperature controller/thermocouple. A mixture of alkanolamines (sold under the tradename AMIX DA5) comprising 2-[2-(dimethylamino)ethoxy] ethanol (about 60% to about 80%), 2-dimethylaminoethanol (about 15% to about 30%), ethyleneglycol (about 3% to about 7%), 2-(ethenyloxy)ethanol (about 1% to about 5%), and water (about 0.5% to about 1.5%). Additional experiments were also carried out using these same protocols where a mixture of alkanolamines was not used but instead, a pure alkanolamine was used, such as 2-[2-(dimethylamino) ethoxy]ethanol or 2-dimethylaminoethanol. 1 Equivalent of alkanolamine or the alkanolamine mixture was used, based on fatty acid. The pure alkanolamine or Amix DA5 was added portion-wise to the reaction and a small exotherm was noted (~15° C.). A Dean-Stark trap and condenser was attached to the flask and the temperature of the reaction was increased to 220° C. over a 3 hour period of time. Water was collected in the trap at temperatures of approximately 120-140° C. After reaching temperature, the reaction was held at 220° C. for 3 hours, followed by cooling, and transferring to a storage container.

Although this synthesis was not carried out as a one-pot process, since multiple alkylation reactions were of interest, the synthesis could be carried out as a one-pot process, as described in the present application. In short, after reaching temperature and holding the reaction for 3 hours at 220° C., the reaction temperature would be reduced to less than 80° C. and the alkyl halide would be added in the one-pot process.

The alkylation was performed in a Radley apparatus (multiple well reactor where up to six reactions can be completed) by adding about 10 grams of the ester to a 100 ml round bottom flask containing a stir bar. The reaction was stirred at room temperature and the alkyl halide (1 Eq.) was added dropwise. The reaction vessel was fitted with a condenser and heated in the Radley apparatus to 125° C. over a 30-minute period. After reaching 125° C., the temperature was maintained for about 2.5 hours and then the vessel was cooled and the product was transferred to a scintillation vial for storage. A general structure of the corrosion inhibitors prepared according to this example is depicted below, and Table 1 notes the various R groups from the alkyl halides as well as the anion.

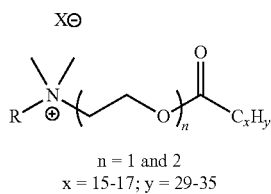

n = 1 and 2
x = 15-17; y = 29-35

TABLE 1

Examples of actives (corrosion inhibitors)

| Example | R | N | X⁻ |
|---------|---|---|-----|
| 1 | benzyl | 1, 2 | Cl |
| 2 | Ethyl | 1, 2 | Br |
| 3 | n-butyl | 1, 2 | Br |
| 4 | ethylacetate | 1, 2 | Cl |
| 5 | propanediol | 1, 2 | Cl |
| 6 | benzyl | 1, 2 | Cl |
| 7 | Ethyl | 1, 2 | Br |
| 8 | n-butyl | 1, 2 | Br |
| 9 | ethylacetate | 1, 2 | Cl |
| 10 | propanediol | 1, 2 | Cl |
| 11 | benzyl | 1, 2 | Cl |
| 12 | Ethyl | 1, 2 | Br |
| 13 | n-butyl | 1, 2 | Br |
| 14 | ethylacetate | 1, 2 | Cl |
| 15 | propanediol | 1, 2 | Cl |
| 16 | benzyl | 1, 2 | Cl |
| 17 | Ethyl | 1, 2 | Br |
| 18 | n-butyl | 1, 2 | Br |
| 19 | ethylacetate | 1, 2 | Cl |
| 20 | propanediol | 1, 2 | Cl |
| 21 | benzyl | 1, 2 | Cl |
| 22 | Ethyl | 1, 2 | Br |
| 23 | n-butyl | 1, 2 | Br |
| 24 | ethylacetate | 1, 2 | Cl |
| 25 | propanediol | 1, 2 | Cl |

Sample Preparation

Each of the examples (1-25) was prepared by diluting the corrosion inhibitor to 20% activity into 2-propanol and formulating with the mercaptan synergist 2-mercaptoethanol (about 20% active CI, about 3.5% synergist, and balance 2-propanol). Each of the examples exhibited solubility in 2-propanol and were evaluated in a continuous wheel box test. This test provides an indication of how a corrosion inhibitor will perform over a range of dosages by measuring the weight loss of a corrosion coupon at each dosage and comparing to uninhibited samples. Corrosion inhibitors, which provide comparable corrosion performance in the wheel box test to the incumbent actives, were further evaluated in a bubble test to compare the actives ability to partition from an oil phase to an aqueous phase using electrochemical techniques.

Wheel Box Test Procedure

In order to evaluate each of the examples, wheel box testing from NACE publication ID182 (December 1982) was performed. The wheel box test is a test often used in the field of corrosion to compare the performance of a corrosion inhibitor to a different corrosion inhibitor. To test corrosion inhibitor performance, the following standard set of conditions was used.

T=176° F.
Oil=10% LVT-200

Brine=90% ASTM Seawater brine
Saturated $CO_2$
Test Duration=24 hrs.
Inhibitor Dosage=10, 25, 50, and 100 ppm based on total fluids The performance of the corrosion inhibitors was evaluated relative to an average corrosion rate of three uninhibited samples. These untreated bottles exhibit much higher corrosion rates than the treated bottles. This allows the corrosion inhibitors to be evaluated by their relative percent protection.

Bubble Cell Test Procedure

The bubble test was designed to evaluate the partitioning properties of new formulations, i.e., how quickly and to what extent in the multiphase system the chemicals will enter the water phase under stagnant conditions where the corrosion reaction takes place. With respect to the field conditions, this test simulates low profile areas, such as dead legs and water traps where no or very limited mixing exists, and the performance of an inhibitor is primarily determined by its capability to partition into the water phase. A synthetic or produced field brine is placed in a specially designed glass kettle where it is stirred at a low speed using a magnetic stir bar. The solution in the kettle is purged with the test gas (such as $CO_2$ when simulating sweet systems) and heated to the test temperature. The corrosion rate is measured by a Linear Polarization Resistance (LPR) technique. An electrochemical probe accommodating three steel electrodes is used to obtain the values of polarization resistance, $R_p$. The data acquisition software converts the data obtained into the corrosion rate in mils per year (mpy). After the probe has been immersed into the brine, a measured volume of crude oil or synthetic hydrocarbon simulating an oil-phase is carefully introduced on top of the brine and the measurement is started. Typically, the system is allowed to equilibrate for several hours during which time the uninhibited corrosion rate baseline is obtained. Then, an inhibitor is injected into the hydrocarbon phase so that it must migrate through the oil into the aqueous phase. A typical testing time period is 24 hours, however, experiments can be run for up to several days.

Corrosion Inhibition Results
Wheel Box Test

Tables 2-6 contain the results from the wheel box test. As can be seen, each of the examples exhibits performance at dosages as low as 10 ppm and many perform increasingly well as the dosages approach 100 ppm. Of particular note, examples 11, 12, and 13 provide superior performance to the incumbent actives under the conditions specified above. These actives were further evaluated in the bubble test for partitioning performance.

TABLE 2

Wheel Box testing results for Examples 1-5

| Example | Concentration, ppm | % Protection |
|---|---|---|
| 1 | 10 | 50.67 |
| 1 | 25 | 62.80 |
| 1 | 50 | 62.95 |
| 1 | 100 | 85.14 |
| 2 | 10 | 53.88 |
| 2 | 25 | 62.36 |
| 2 | 50 | 65.00 |
| 2 | 100 | 83.91 |
| 3 | 10 | 39.62 |
| 3 | 25 | 54.94 |
| 3 | 50 | 71.46 |
| 3 | 100 | 81.55 |
| 4 | 10 | 38.44 |
| 4 | 25 | 53.67 |
| 4 | 50 | 54.47 |
| 4 | 100 | 71.15 |
| 5 | 10 | 44.38 |
| 5 | 25 | 47.57 |
| 5 | 50 | 58.99 |
| 5 | 100 | 62.52 |

TABLE 3

Wheel Box testing results for Examples 6-10

| Example | Concentration, ppm | % Protection |
|---|---|---|
| 6 | 10 | 61.00 |
| 6 | 25 | 63.42 |
| 6 | 50 | 79.70 |
| 6 | 100 | 86.94 |
| 7 | 10 | 55.56 |
| 7 | 25 | 70.10 |
| 7 | 50 | 81.77 |
| 7 | 100 | 86.88 |
| 8 | 10 | 41.75 |
| 8 | 25 | 70.78 |
| 8 | 50 | 73.97 |
| 8 | 100 | 82.73 |
| 9 | 10 | 48.50 |
| 9 | 25 | 51.59 |
| 9 | 50 | 65.52 |
| 9 | 100 | 84.65 |
| 10 | 10 | 34.35 |
| 10 | 25 | 58.19 |
| 10 | 50 | 56.52 |
| 10 | 100 | 73.01 |

TABLE 4

Wheel Box testing results for Examples 11-15

| Example | Concentration, ppm | % Protection |
|---|---|---|
| 11* | 10 | 61.20 |
| 11* | 25 | 85.10 |
| 11* | 50 | 91.46 |
| 11* | 100 | 91.72 |
| 12* | 10 | 62.36 |
| 12* | 25 | 82.90 |
| 12* | 50 | 90.19 |
| 12* | 100 | 94.08 |
| 13* | 10 | 61.52 |
| 13* | 25 | 75.92 |
| 13* | 50 | 91.35 |
| 13* | 100 | 91.76 |
| 14 | 10 | 24.98 |
| 14 | 25 | 65.18 |
| 14 | 50 | 75.49 |
| 14 | 100 | 75.49 |
| 15 | 10 | 53.02 |
| 15 | 25 | 52.43 |
| 15 | 50 | 71.09 |
| 15 | 100 | 80.87 |

*Average results from three tests.

TABLE 5

Wheel Box testing results for Examples 16-20

| Example | Concentration, ppm | % Protection |
|---|---|---|
| 16 | 10 | 55.97 |
| 16 | 25 | 55.94 |
| 16 | 50 | 59.03 |
| 16 | 100 | 93.04 |
| 17 | 10 | 33.48 |
| 17 | 25 | 66.21 |
| 17 | 50 | 84.58 |
| 17 | 100 | 85.19 |
| 18 | 10 | 56.78 |
| 18 | 25 | 69.47 |
| 18 | 50 | 68.52 |
| 18 | 100 | 88.12 |
| 19 | 10 | 63.10 |
| 19 | 25 | 63.01 |
| 19 | 50 | 61.34 |
| 19 | 100 | 71.75 |
| 20 | 10 | 47.32 |

TABLE 5-continued

Wheel Box testing results for Examples 16-20

| Example | Concentration, ppm | % Protection |
|---|---|---|
| 20 | 25 | 57.25 |
| 20 | 50 | 58.67 |
| 20 | 100 | 69.52 |

TABLE 6

Wheel Box testing results for Examples 21-25

| Example | Concentration, ppm | % Protection |
|---|---|---|
| 21 | 10 | 52.35 |
| 21 | 25 | 59.87 |
| 21 | 50 | 77.07 |
| 21 | 100 | 74.07 |
| 22 | 10 | 55.02 |
| 22 | 25 | 63.62 |
| 22 | 50 | 78.76 |
| 22 | 100 | 79.04 |
| 23 | 10 | 53.02 |
| 23 | 25 | 58.81 |
| 23 | 50 | 60.20 |
| 23 | 100 | 65.29 |
| 24 | 10 | 53.36 |
| 24 | 25 | 53.55 |
| 24 | 50 | 63.43 |

TABLE 6-continued

Wheel Box testing results for Examples 21-25

| Example | Concentration, ppm | % Protection |
|---|---|---|
| 24 | 100 | 77.35 |
| 25 | 10 | 53.05 |
| 25 | 25 | 54.19 |
| 25 | 50 | 51.82 |
| 25 | 100 | 59.81 |

Bubble Cell Test

Each of the examples provides excellent partitioning into the 3% seawater brine (see Table 7). The new actives significantly outperform the incumbent actives in this evaluation. Conditions for the test are as follows:

T=80° C.
Oil=10% LVT-200
Brine=90%-3% NaCl brine
Saturated $CO_2$
Test Duration=24 hrs.
Inhibitor Dosage=10 ppm based on total fluids

TABLE 7

Bubble Cell Results
Bubble Cell Results

| Example | Dosage (ppm) | Baseline (mpy) | 2 hrs after dosing mpy | 2 hrs after dosing % Protection | 8 hrs after dosing mpy | 8 hrs after dosing % Protection | 20 hrs after dosing mpy | 20 hrs after dosing % Protection |
|---|---|---|---|---|---|---|---|---|
| 0 | 0 | 200.6 | 240.8 | NA | 282.4 | NA | 302.8 | NA |
| 0 | 0 | 200.1 | 260.7 | NA | 339.2 | NA | 413.3 | NA |
| 11 | 10 | 186.5 | 22.2 | 88.1 | 11.7 | 93.7 | 10.5 | 94.4 |
| 11 | 10 | 178.9 | 21.9 | 87.8 | 11.9 | 93.3 | 13.6 | 92.4 |
| 12 | 10 | 191.5 | 29.2 | 84.8 | 23.5 | 87.7 | 23.9 | 87.5 |
| 12 | 10 | 207.7 | 35.8 | 82.8 | 21.0 | 89.9 | 18.0 | 91.3 |
| 13 | 10 | 235.1 | 25.7 | 89.1 | 13.7 | 94.2 | 11.9 | 94.9 |
| 13 | 10 | 206.7 | 31.0 | 85.0 | 22.0 | 89.4 | 21.2 | 89.7 |

As can be seen in Table 8, the presently disclosed corrosion inhibitor compositions have higher performance in the continuous wheel box test than the incumbents.

TABLE 8

Wheel Box Data Comparison to Incumbent (Benzyl Quat)
Wheel Box Data Comparison to Incumbent Active - Benzyl Quat

| | Dosage | % Protection |
|---|---|---|
| Active Formulation #1 | 10 | 73.94% |
| Benzyl Ester Quat | 25 | 88.59% |
| | 50 | 89.55% |
| | 100 | 90.95% |
| Benzyl Quat Formulation | 10 | 44.50% |
| | 25 | 85.44% |
| | 50 | 89.03% |
| | 100 | 92.06% |

Further, as seen in Table 9, the bubble cell test data indicates that the presently disclosed corrosion inhibitors are superior to the current quaternary corrosion inhibitors utilized in the oilfield.

TABLE 9

Bubble Test Data Comparison
Bubble Test Data Comparison to Incumbent Methyl ester quat

| Chemical | Dosage (ppm) | Baseline (mpy) | 2 hrs after dosing | | 8 hrs after dosing | | 17.5 hrs after dosing | |
|---|---|---|---|---|---|---|---|---|
| | | | mpy | % Protection | mpy | % Protection | mpy | % Protection |
| Methyl Ester Quat | 10 | 208.1 | 159.6 | 23.3 | 166.0 | 20.2 | 180.4 | 13.3 |
| Methyl Ester Quat | 10 | 211.4 | 135.5 | 35.9 | 140.0 | 33.8 | 153.4 | 27.4 |
| Our Ester Quat #1 | 10 | 195.6 | 36.1 | 81.5 | 25.9 | 86.8 | 30.4 | 84.5 |
| Our Ester Quat #1 | 10 | 203.1 | 52.1 | 75.0 | 45.9 | 77.9 | 48.0 | 76.9 |

In addition to the foregoing beneficial technical effects, the corrosion inhibitor compositions presented herein have superior biodegradability and toxicity profiles than current corrosion inhibitors. The present corrosion inhibitors also have improved stability at lower temperatures and flocculation or precipitation in corrosion inhibitor product can be eliminated by using the present corrosion inhibitors. Moreover, the raw materials utilized in the synthesis may be obtained from waste streams and therefore can have a cost advantage compared to "pure" materials.

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a corrosion inhibitor composition" is intended to include "at least one corrosion inhibitor composition" or "one or more corrosion inhibitor compositions."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. A corrosion inhibitor composition comprising a corrosion inhibitor having the following general structure:

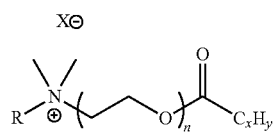

wherein n is 1 or 2; x is 1, 2, 3, 4, 5, 6, 7, 8, 9, 10, 11, 12, 13, 14, 15, 16, 17, 18, 19, 20, 21, or 22; y is an integer corresponding to a number of hydrogen atoms necessary for each carbon of the $C_xH_y$ group to form four covalent bonds; R is H, a benzyl group, a linear alkyl group, or a branched alkyl group; and $X^-$ is an anion.

2. The composition of claim 1, wherein the $C_xH_y$ group of the general structure is selected from the group consisting of a linear alkyl group, a branched alkyl group, a cyclic alkyl group, a saturated alkyl group, and an unsaturated alkyl group.

3. The composition of claim 1, wherein the $C_xH_y$ group is selected from the group consisting of $C_{17}H_{35}$, $C_{17}H_{33}$, $C_{17}H_{31}$, $C_{17}H_{29}$, $C_{15}H_{31}$, $C_{15}H_{29}$, $C_{13}H_{27}$, $C_{13}H_{25}$, and $C_{11}H_{23}$.

4. The composition of claim 1, wherein x is 12, 13, 14, 15, 16, 17, or 18.

5. The composition of claim 1, wherein R is selected from the group consisting of ethyl, n-butyl, ethylacetate, and propanediol.

6. The composition of claim 1, wherein the corrosion inhibitor is selected from the group consisting of:

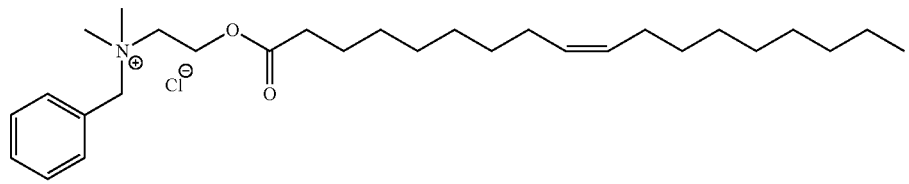

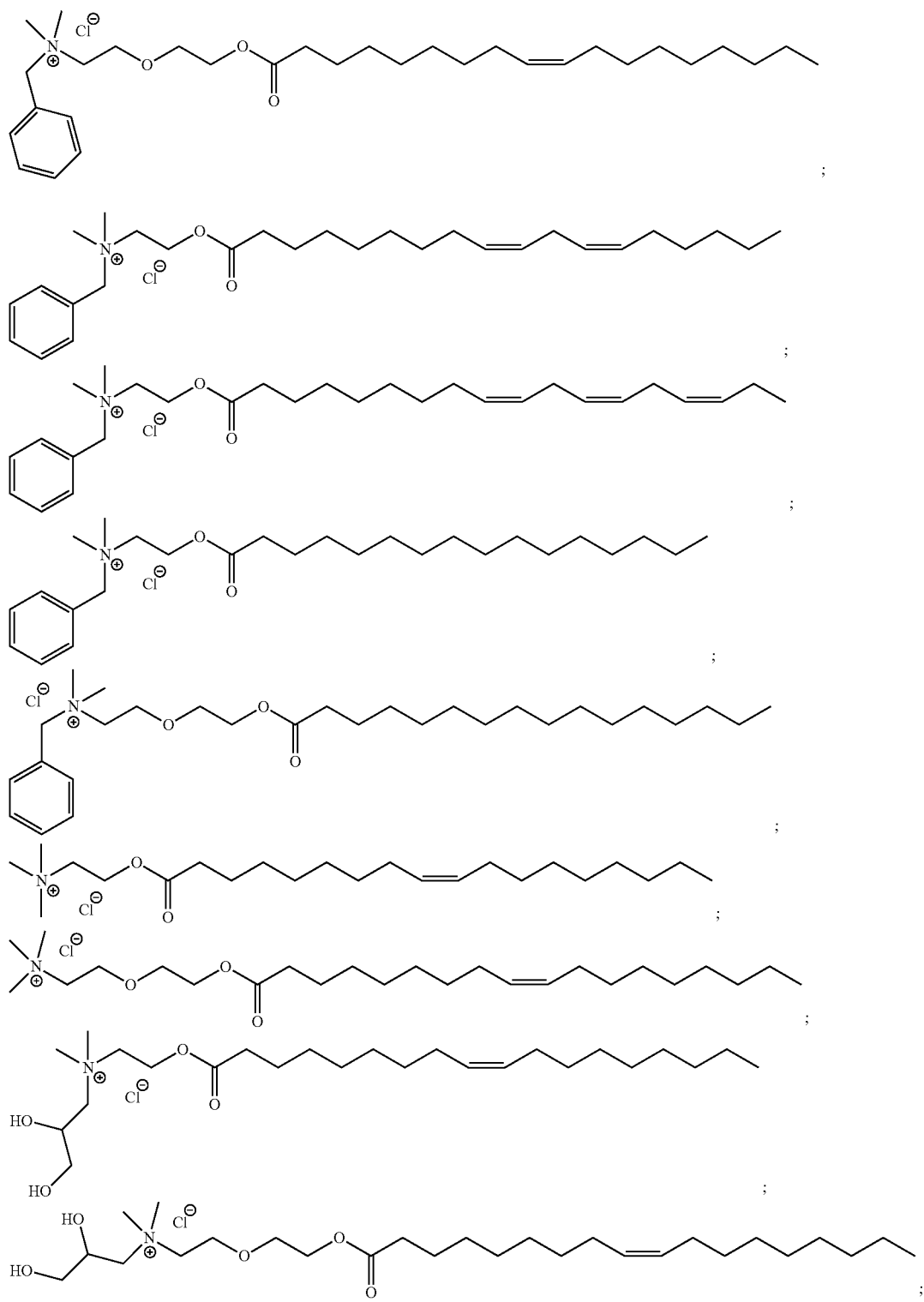

and any combination thereof.

7. A method of inhibiting corrosion comprising adding an effective amount of a composition comprising a corrosion inhibitor comprising a hydrolysable functional group to an aqueous industrial system having at least one surface and inhibiting corrosion of the at least one surface.

8. The method of claim 7, wherein the effective amount is from about 1 ppm to about 200 ppm.

9. The method of claim 7, wherein the aqueous industrial system is selected from the group consisting of water recirculating systems, cooling water systems, boiler water systems, pulp slurries, papermaking processes, ceramic slurries, mixed solid/liquid systems, and oil-field systems.

10. The method of claim 7, wherein the surface comprises a member selected from the group consisting of mild steel, galvanized steel, aluminum, aluminum alloys, copper, copper nickel alloys, copper zinc alloys, brass, chrome steels, ferritic alloy steels, austenitic stainless steels, precipitation-hardened stainless steels, high nickel content steels, and any combination thereof.

11. The method of claim 7, wherein the composition is added to the system manually or automatically.

12. The method of claim 7, wherein the aqueous industrial system is selected from the group consisting of a three phase production system, a two phase production systems, a produced oil system, a water disposal system, a gas condensate system, a gas compressor system, and a lift well system.

13. The method of claim 7, wherein the corrosion inhibitor comprises the following general structure:

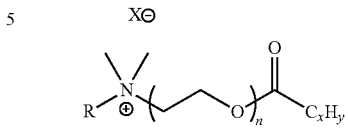

wherein n is 1 or 2; x is 1, 2, 3, 4, 5, 6, 7, 8, 9, 10, 11, 12, 13, 14, 15, 16, 17, 18, 19, 20, 21, or 22; y is an integer corresponding to a number of hydrogen atoms necessary for each carbon of the $C_xH_y$ group to form four covalent bonds; R is H, a benzyl group, a linear alkyl group, or a branched alkyl group; and $X^-$ is an anion.

14. The method of claim 7, wherein the corrosion inhibitor is selected from the group consisting of:

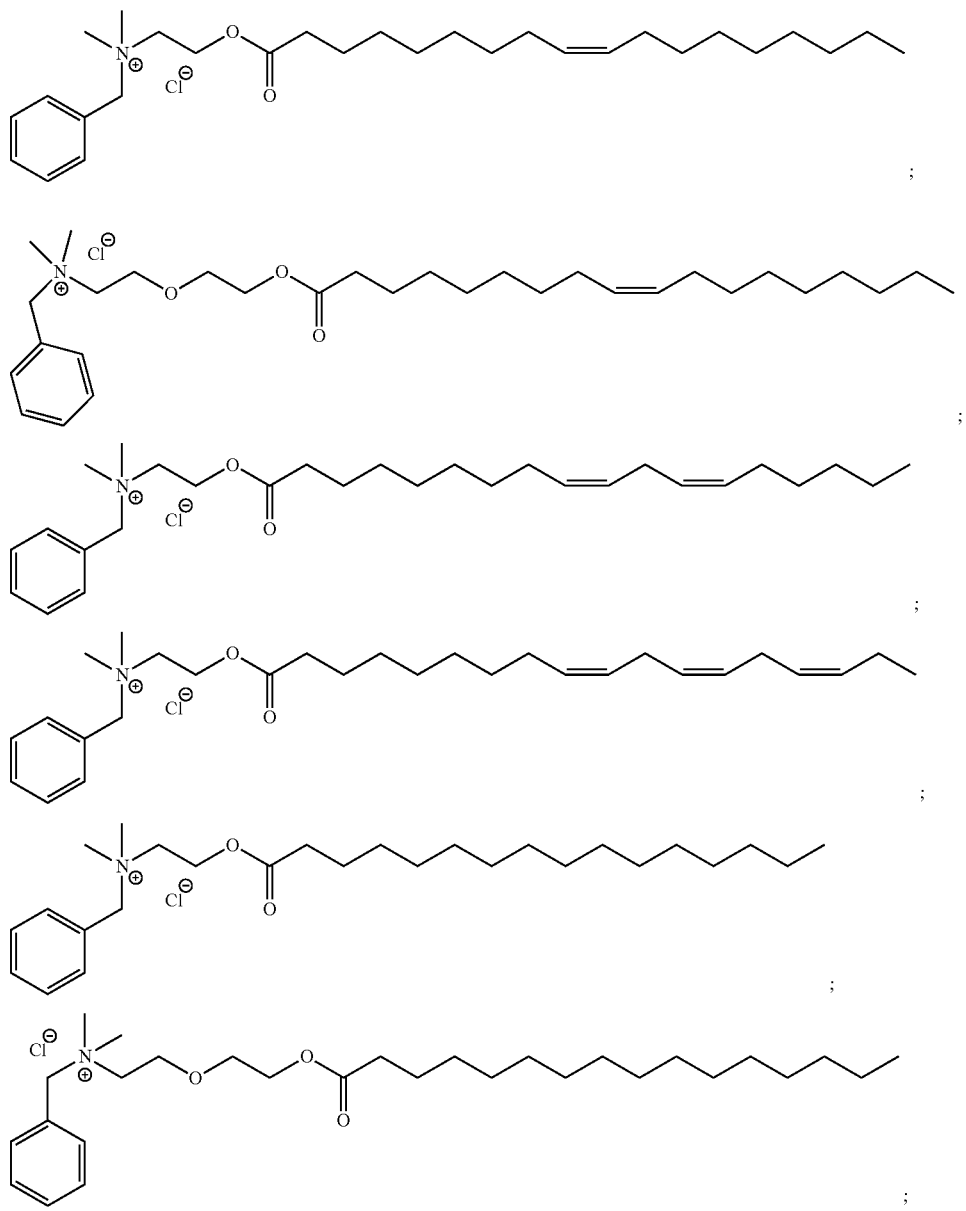

-continued

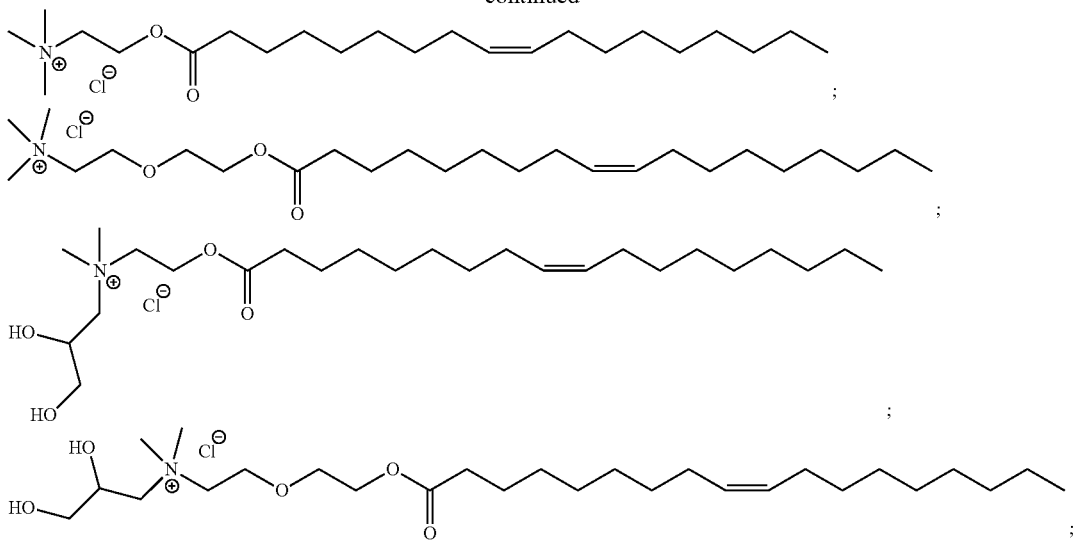

and any combination thereof.

15. A method of manufacturing a composition comprising a quaternary ammonium corrosion inhibitor comprising:
   reacting an alkanolamine with a fatty acid in a reaction vessel to form a fatty acid ester reaction product; and
   reacting the fatty acid ester reaction product with an alkyl halide or an acrylate in the reaction vessel, thereby forming the quaternary ammonium corrosion inhibitor.

16. The method of claim 15, wherein the alkanolamine is selected from the group consisting of 2-[2-(dimethylamino)ethoxy]ethanol, 2-dimethylaminoethanol, and any combination thereof.

17. The method of claim 15, wherein the fatty acid is selected from the group consisting of tall oil fatty acid, soya fatty acid, oleic acid, linoleic acid, linolenic acid, coco fatty acid, stearic acid, palmitic acid, lauric acid, capric acid, myristic acid, arachidic acid, and any combination thereof.

18. The method of claim 15, wherein the alkyl halide is selected from the group consisting of benzyl chloride, methyl chloride, ethyl chloride, propyl chloride, butyl chloride, hexyl chloride, chloropropanediol, ethylchloroacetate, and bis(2-chloroethyl)ether.

19. The method of claim 15, wherein the reaction vessel does not comprise a solvent.

20. The method of claim 15, further comprising the steps of:
   heating the reaction vessel from about 150° C. to about 250° C. for about 3 hours to about 10 hours during the step of reacting the alkanolamine with the fatty acid to form the fatty acid ester reaction product;
   cooling the reaction vessel to below about 80° C.;
   adding the alkyl halide or acrylate to the fatty acid ester reaction product; and
   heating the reaction vessel from about 100° C. to about 150° C. for about 2 hours to about 6 hours.

* * * * *